United States Patent [19]

Levinthal et al.

[11] Patent Number: 4,908,781
[45] Date of Patent: Mar. 13, 1990

[54] COMPUTING DEVICE FOR CALCULATING ENERGY AND PAIRWISE CENTRAL FORCES OF PARTICLE INTERACTIONS

[75] Inventors: Cyrus Levinthal; Richard M. Fine, both of New York, N.Y.

[73] Assignee: The Trustees of Columbia University in the City of New York, New York, N.Y.

[21] Appl. No.: 796,870

[22] Filed: Nov. 12, 1985

[51] Int. Cl.⁴ .............................................. G06F 15/52
[52] U.S. Cl. ...................................... 364/524; 364/527
[58] Field of Search ............... 364/524, 496, 813, 814, 364/815, 527

[56] References Cited

U.S. PATENT DOCUMENTS

| | | | |
|---|---|---|---|
| 4,282,006 | 8/1981 | Funk | 406/197 |
| 4,327,288 | 4/1982 | Ashkin et al. | 250/251 |
| 4,399,047 | 8/1983 | Seiver et al. | 252/62.55 |
| 4,442,019 | 4/1984 | Marks | 350/362 |
| 4,554,088 | 11/1985 | Whitehead et al. | 252/62.51 R |
| 4,627,040 | 6/1987 | Josephson | 252/62.51 |
| 4,704,692 | 11/1987 | Ladner | 364/498 X |

Primary Examiner—Parshotam S. Lall
Assistant Examiner—Edward R. Cosimano
Attorney, Agent, or Firm—John P. White

[57] ABSTRACT

This invention provides a computing device which calculates the total energy and total pairwise, central forces between selected pairs of interacting particles within a system. The device comprises (a) a means for generating both (i) a retrievable identifier for the spatial coordinates (x, y, z) of a particle i and (ii) retrievable identifiers of the type of pairwise, central interaction between i and a second particle j; (b) a means for determining $r^2$, the square of the radius vector between i and j; (c) a means for determining r, the square root of $r^2$; (d) a means for calculating energy and force/r values for each ij pair; (e) means for determining the force on each particle; and (f) means for accumulating energy and force/r values for each ij particle pair.

12 Claims, 3 Drawing Sheets

COMPUTING DEVICE FOR CALCULATING ENERGY AND PAIRWISE CENTRAL FORCES OF PARTICLE INTERACTIONS

BACKGROUND OF THE INVENTION

This invention was made with government support under Grant Number NIH 1P41-RR02554 from the National Institute of Health and NSF PCM 84-02496 from the National Science Foundation. The U.S. government has certain rights in this invention.

Throughout this application various publications are referenced by number within parentheses. Full citations for these publications may be found at the end of the specifications immediately preceding the claims. The disclosures of these publications in their entireties are hereby incorporated by reference into this application in order to more fully describe the state of the art to which this invention pertains.

The computational aspect of molecular modelling has received increasing attention from many investigators during the past several years (1). This is due not only to the great progress made since the 1950's in conventional protein crystallography but is also due to the promise of protein structure determination using synchrotron radiation and to the availability of new kinds of information from the use of neutron and electron diffraction and 2-D nuclear magnetic resonance (2). The application of improved computational techniques for molecular dynamics and energy minimization to proteins, to liquids and gases, to foreign atoms in solids, and to the interactions between molecules have all contributed to the use of very large amounts of computer time (3). In these calculations the time required is used primarily to determine the energy and force on each atom due to its interaction with all of the others. Much less time is needed to calculate the displacements which each atom should undergo because of the forces and the past history of the energy, forces and velocities of the particles.

It is obvious that increasing by a thousand fold the speed of computer programs which require large amounts of time will have significant effect on the nature of the problems which can be dealt with successfully. To make this statement more explicit, a description of some of the problems which are now being pursued and the impact that this invention would have on them is described herein. Further, some of the other problems which are now using large amounts of computer time and for which this invention will have a significant impact are discussed herein.

Modelling of the combining sites of antibody molecules has become a particularly important problem in recent years because it is now possible to obtain the amino acid sequence of monoclonal antibodies relatively easily by sequencing the cDNA which encodes the protein (15). Further, it is now possible to alter a portion of the peptide or complemetarity determining region by manipulating cloned cDNA. Thus, it is in principal possible to change the amino acid sequence in such a way that the molecule has an altered combining affinity. The questions being asked are whether one can understand the structure-function relationships well enough to predict the conformation of the combining site from the amino acid sequence alone, and whether one can predict changes in the binding affinity and selectivity when specific mutations are introduced by in vitro mutagenesis.

A second problem which is currently being investigated is the 3-D structure of the portion of the colicin El protein which produces an ion channel through a biological membrane (16). The work involves extensive protein model building and efforts to predict changes in the electro-physiological properties of the protein when the amino acid sequence is changed by in vitro mutagenesis.

Investigations in which features of the 3-D structure and the function of proteins from the amino acid sequence or changes in the sequence are studied also require large amounts of computer time (7,18). It is practical with the VAX to find a minimum energy conformation which is at the bottom of whatever local energy valley one happens to start in. But, even for a small portion of a complete protein, enormous amounts of computer time are needed if one wishes to explore a significant region of conformation space. For example, in order to find a reasonable packing arrangement for the antibody combining sites, it is necessary to start with many different conformations and for each to carry out a process of minimizing the packing energy. The starting conformations can be obtained either by a random or a systematic alteration of the structure to be minimized. Alternatively, one can use a molecular dynamics program to explore a space and use the results to aid in the search for a global minimum.

Even with the device presented herein, the time required to find the global minimum for an entire protein from the amino acid sequence alone would be prohibitive. However, for the antibody combining site, for the colicin channel, or for enzymes whose structures have been solved crystallographically, it should be possible to explore the changes induced by mutation. In the case of antibodies it is reasonable to explore the possible combining site conformations, given the structure of the framework region in which the complimentary-determining regions are embedded, since they are the same for all antibody molecules.

Another class of problems which has not been approachable until now involves understanding the details of the passage of ions through channels, the specificity of channels and the interaction of portions of a protein with water molecules on the exterior (19). In the case of the colicin El channel, for example, neither the observed value of its conductance or the ion specificity is understood in detail. It is our expectation that applying molecular dynamics to the water, the ions, and the amino acid side-chains facing into the channel will contribute greatly to the understanding of how the channel functions.

There are several disciplines in addition to protein physical chemistry which should benefit from the device of this invention. This device is applicable to any many-body problem subject to central forces. Such problems arise in many fields of science and engineering, ranging from astronomy through solid-state and plasma physics to biology and chemistry.

The design of pharmaceutical drugs would be enhanced by the type of computer simulations possible using this device. In the past, drug companies have proceeded with their goal of developing new drugs by the method of "blind" analog development. Given a successful drug, new drugs have been tried by manually synthesizing hundreds or thousands of analogs for testing by injection into test animals. The energies of the computational capabilities of molecular dynamics; Monte Carlo, energy minimization; and template forces searching etc., have enhanced the possibility for a new approach to the entire problem, called "rationalized" drug design. Briefly, and ideally, the approach involves the design and screening of drugs by computer simulation at the atomic level with a description of the interaction of a drug with its receptor site. This can be done if the structure of the receptor site is known by, for example, x-ray crystallography. The predicted change in the binding constant of a new analog to the site is approachable by using free energy, simultations, and slowly mutating the structure of the old drug whose binding is known into the structure of a new and better drug. Other kinds of energetic manipulations on both the analogue and the protein can provide extremely valuable guidance not only for computer screening of analogs but also for suggesting new directions for drug development which might not have been obvious without the simulational tools.

Similarly, energy minimization calculation can be used to tackle issues in protein engineering. To take full advantage of the emerging technology of recombinant DNA requires the development of predictive capability: e.g., if one modifies the gene which codes for the light chain of an antibody molecule, can one predict what change this will have on the function of that antibody? If one modifies the gene for a nerve channel protein, can one design organisms with modified nervous system response? If one modifies the gene for photoreceptors, can one turn the sensitivity to new ranges of wavelengths, extending vision into the near infrared? All of these problems, as well as others, can be, and are, under active investigation in various laboratories, both in industry and at universities. However, the computations involved in tackling energy minimization calculations for biologically interesting molecules can be prohibitive.

SUMMARY OF THE INVENTION

The invention concerns a computing device which calculates the energy and pairwise, central forces between pairs of discrete interacting particles.

The components include a means for generating a retrievable identifier for the spatial coordinates (x, y, z) of a first particle (i), e.g. an oxygen atom with coordinates (2,4,2), and a means for identifying the type of pairwise, central relationship between i and a second particle or group (j), e.g., when j is a carbon atom the relationship is an oxygen-carbon interaction. These means are responsive to the generation of digital words from an external word generator.

The components also include a means for determining the square of the radius vector ($r^2$), e.g., for any particle with coordinates (a,b,c) and a second particle with coordinates (a',b',c') the equation for $r^2 = (a-a')^2 + (b-b')^2 + (c-c')^2$. This calculation is performed with a system of subtracters and multipliers responsive to digital words describing the spatial coordinates of any i and j, and the solution, $r^2$, l is sent in digital word form to a means for calculating r.

A means for calculating the square root of $r^2$ is also a component of the computing device. This means is responsive to a digital word for the value of $r^2$ and comprises a quadratic look-up table which gives a value of r for the corresponding $r^2$, and outputs the r so obtained as a digital word.

A means for calculating the energy and force/r for an ij pair is also a component of the device. This means contains quadratically-interpolated tables which are responsive to digital words describing the ij pair type and the value of r. These digital words are entered into the formula:

E = Cf1(pt) * Table 1(pt,r) + Cf2(pt) * Table 2(pt,r)

A solution for the total energy of the ij pair is sent as a digital word to an energy accumulating memory. A solution for force/r is sent as a digital word to a force/r accumulating memory.

A means for accumulating energy values is also a component of the device. This means sums energy for each ij formed by a given i, and comprises an adder responsive to digital word input obtained as solutions of the energy formula.

A means for accumulating force/r for each i and j of each and all ij pairs is also a component of the device. This means is responsive to digital words for solutions to the force/r equation, and forms a product of each solution and the difference of each dimensional coordinate of the ij pair, e.g. (force/r)(a-a') and (force/r)(b-b') and (force/r)(c-c') when the coordinates of i and j are (a,b,c) and (a',b',c'), respectively. These products are then summed to the existing force/r for i and added as negative values to the total force/r for j.

Finally, a molecular mechanics calculating device for molecular conformation studies is described. This device comprises a means for generating a retrievable identifier for the spatial coordinates (x, y, z) of a first atom; and for identifying the type of pairwise, central relationship between i and a second defined particle j, thereby defining an ij pair, a means for determining the square of the radius vector $r^2$ between atoms i and j, a means for determining the square root of $r^2$, a means for calculating the energy and magnitude of force/r for any defined ij pair when r is known, and a means for accumulating energy and force/r for each i and j.

DETAILED DESCRIPTION OF THE INVENTION

Figure 2:
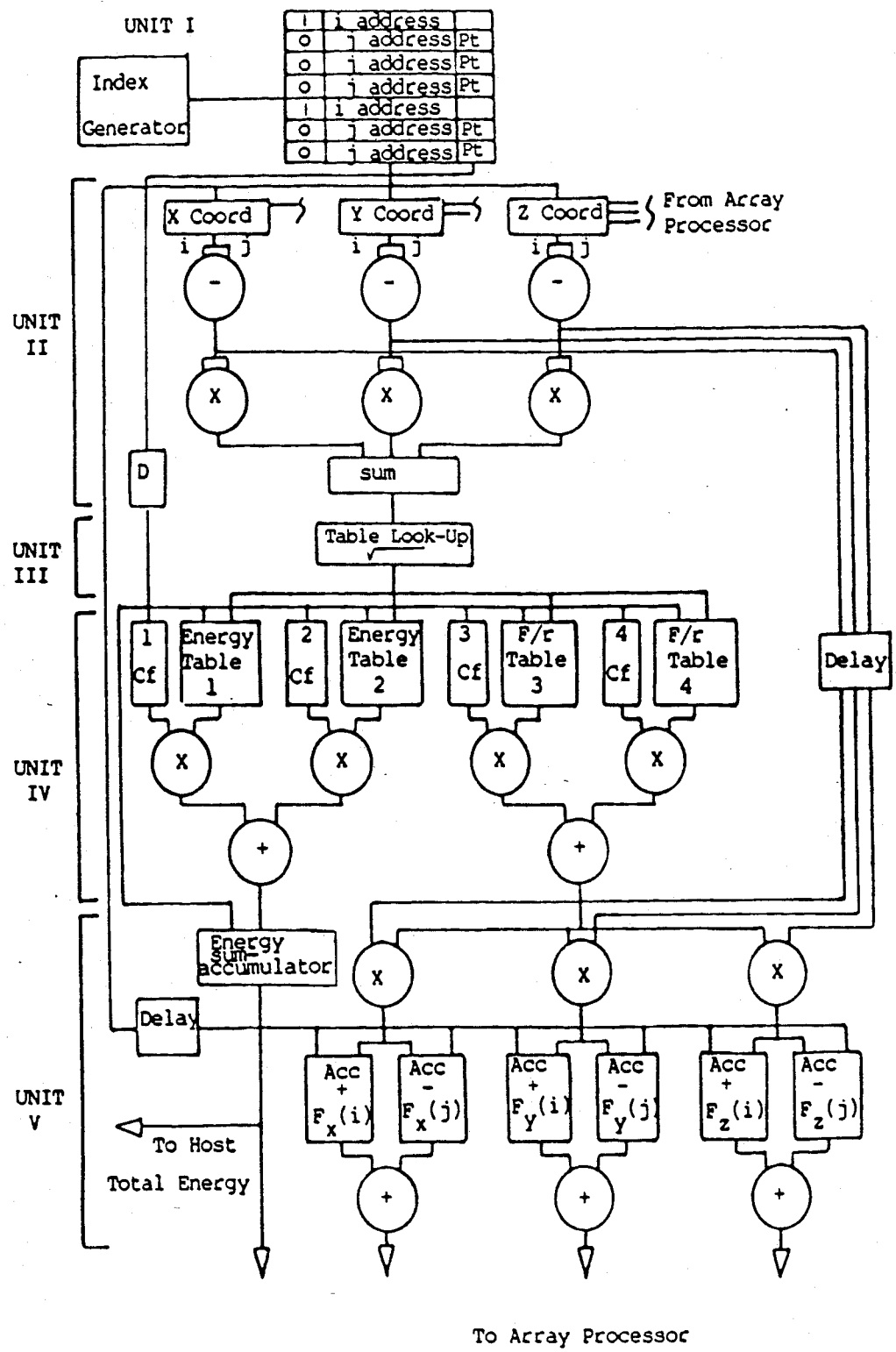
FIG. 2. General Schematic of the Computing Device of this Invention.

The processor can functionally be broken into five units, as shown in FIG. 2:

Unit I: The Neighbor List. This contains the addresses necessary to look up the coordinates of the individual atoms; an ij bit which identifies an atom as an i or a j atom; and a pair type, which indicates the type of pair a atom forms with the most recently accessed i atom. Each clock cycle, these three atom oriented pieces of information are delivered to the other units.

Unit II: The r Squared Calculation. This unit contains the coordinate memories, and the associated hardware to calculate $$r^2 = (x_i - x_j)^2 + (y_i - y_j)^2 + (z_i - z_j)^2$$

Unit III: The r Calculation. This unit performs a quadratic table look-up to obtain the value of r, given the value of r squared.

Unit IV: The Energy and Force/r Tables. This unit contains the quadratically-interpolated tables used to look up the energy and the magnitude of the force/r between a j atom and the most recently considered i atom. The Energy and the Force/r sections are identical, and consist of weighted sums of two contributions: for the Energy, E = ACoeff*(Table A)+BCoeff*(Table B).

The coefficient tables A, B, C, and D contain information relating to the products of the partial charges $(q_1 \times q_2)$ on the atoms and information relating to the van der Waals forces, as is well known.

Unit V: The Energy and Force Accumulators. This unit contains sum accumulation memories which accumulate the total energies associated with a few selected classes of atoms and the total force components associated with each atom. The components are calculated by multiplying F/r by $(x_i-x_j)$ to obtain $F_x$, etc.

Throughout the diagram, various delays, either labelled "Delay" or "D", have been indicated. These are either file register delays (where the delays are long) or shift register delays (where the delays are short). These delays guarantee the arrival of information pertaining to a given pair at the appropriate input to a unit in synch.

Figure 3:
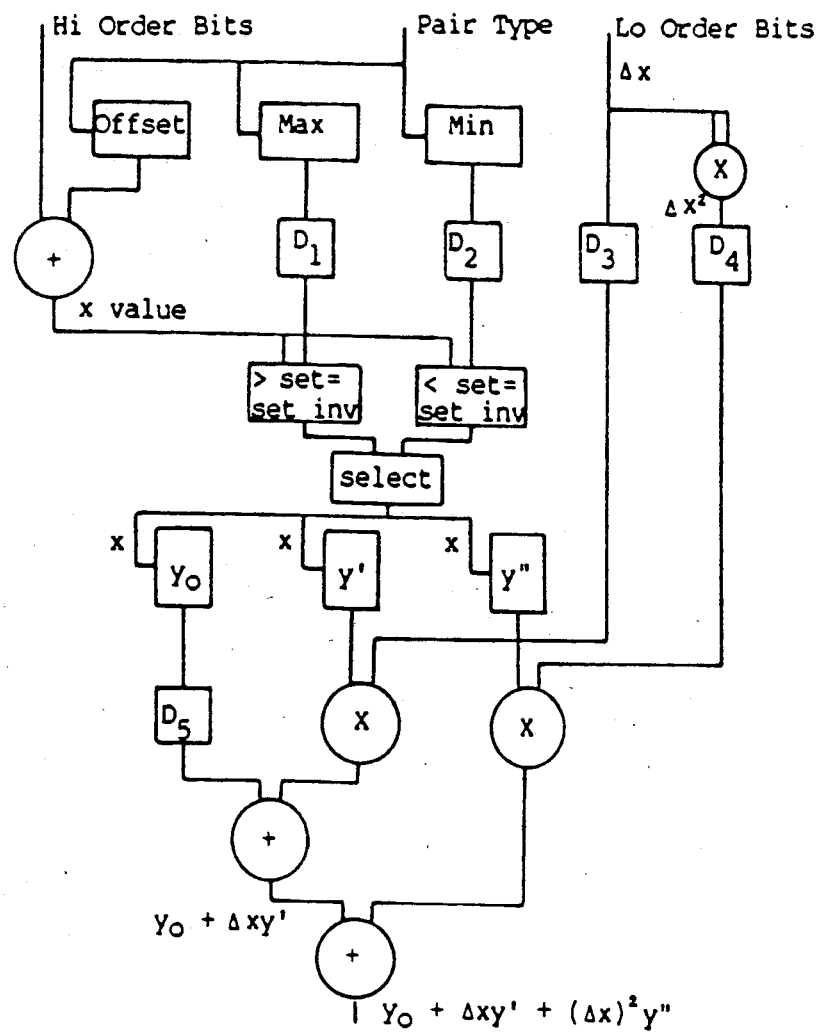
FIG. 3. Schematic of the Quadratic Interpolators.

The quadratic interlopers, shown schematically in FIG. 3, are used to look up the values of the energy, the force/r, and the square root. The central memories, $y_0$, $y'$, and $y''$, contain tables of the functional values, slopes, and ½ times the second derivatives of the desired function. The beginning of the appropriate table for a given pair type is stored in an offset memory. This offset is added to the high order bits of the incoming(integer) independent parameter, and the result is used to address the central memories. This value is represented by the letter x in the figure. The adders and multipliers form the combination $$y = y + y_O + (d_x)(y' + d_x(Y''))$$

where d consists of the low order bits of the independent parameter. It is understood that the Notation dx represents delta x; which is, for example, the output of the x-coordinate subtractor in FIG. 2. There are also two memories, Max and Min, which store the maximum and minimum addresses of the tables associate with any given pair type. If the generated address falls outside of this range, an "invalid bit" is set.

The invention described herein is designed to be extremely flexible and will serve for any currently addressed problem in molecular mechanics. The flexibility arises from the fact that all function evaluations are done as table look-ups in which the functions and their first and second derivatives are stored in tables which represent a local quadratic fit for each function needed. Since the tables are loaded from the host computer and can be changed to suit a given problem, new force fields can always be accommodated. In addition, the invention is designed to calculate only the force of each atom due to the pairwise interactions, leaving all other calculations to be done in a programmable array processor. The overall system, consisting of the device of this invention, the array processor, a host computer, mass storage, and communications and display hardware, will yield speeds roughly an order of magnitude greater than those available on Cray-1-1S or Cyber 205 for molecular mechanics calculations.

On any general purpose computer, the most time intensive part of the calculation is the evaluation of the interaction energy and the vector forces on each atom. Once the 3N component force vector is formed, a much smaller computation consists of updating the 3N coordinates of the atoms given the forces and total energy. To limit the size of the calculation, most investigators carrying out simulations or minimizations generate a list of atom-pairs which are close enough to each other to be included in the force and energy calculation. The size of these pair-lists or "neighbor" lists depend on the distance cutoff used in the force and energy calculations and may vary for different energy types. The pair-list must be regenerated as the atoms move and the number of interactions, or time steps, between the regenerations will depend on the number of neighbors we assume for each atom. The larger the pair-list, the less often it must be regenerated, and in operation the system will have to be optimized for each problem with respect to pair-list size.

Figure 1:
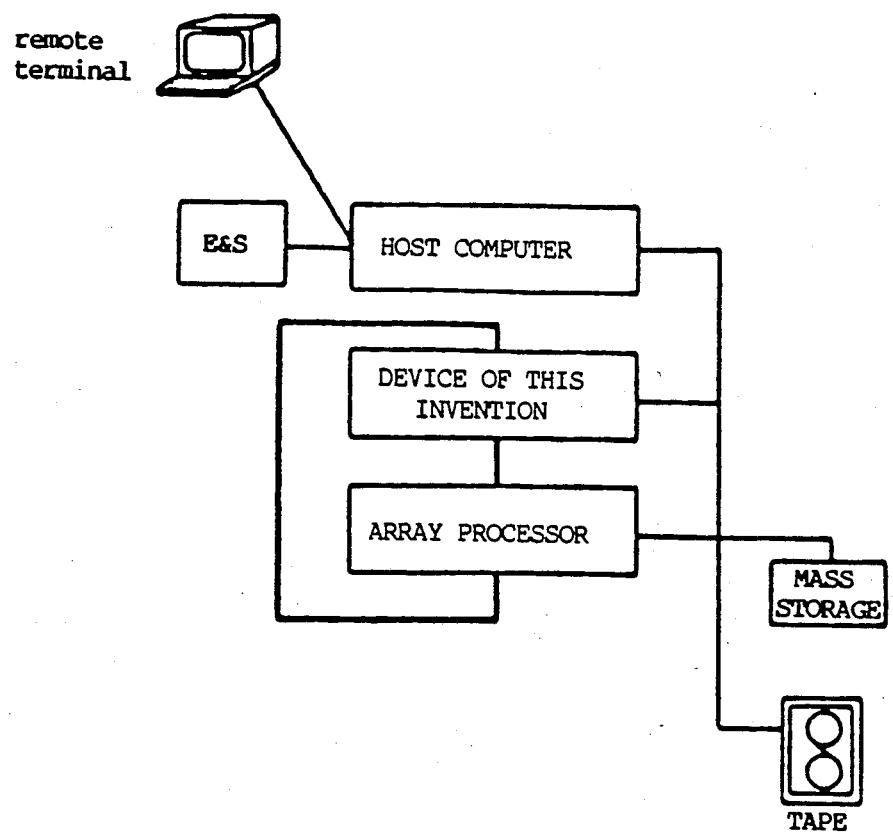
FIG. 1. Overview of the Molecular Mechanics Computing Device.

The overall hardware architecture of the present invention, which mirrors the software architecture described above, is shown in FIG. 1. There are two central modules, one of which is home built and the other of which is a commercially available array processor. The home built module, the device of this invention, calculates the total energy and vector force on each atom due to pairwise forces only. The commercial array processor calculates those forces involving 3 or 4 atoms (torsional terms, angle bending terms, cross terms), and uses these results combined with those from the device of this invention to update the coordinates to a new molecular conformation. Roughly 95% of the time spent in a calculation on a conventional computer is spent evaluating the pairwise forces; as such, this device has been designed to give speeds roughly ten times greater than those available on supercomputers of the Cray-1S class. By concentrating on the pairwise forces, only those portions of the inner loop which are the most time intensive and stable are frozen in hardware. The implementation of the coordinate update in a programmable array processor allows flexibility in tailoring the integration or minimization technique to a specific problem.

The overall schematic of this device is shown in FIG. 2. The architecture adopted is a parallel, synchronous pipeline. Each element in the machine is a multiplier, an adder, or a table look-up. Most arithmetic is done in 32 bit floating point, and is accomplished by utilizing commercially available 32 bit floating point chips recently introduced by the Weitek Corporation. Accumulation of forces and energies is done to higher bit precision, and the pipeline cycle time is 100ns. Each clock cycle, an entry corresponding to an atom is etched from a Pair List Memory. The structure of the pair-list is such that every i atom entry (slow moving index of a j pair) is followed by all j i atom entries (fast moving index) in the list. Each entry (32 bit total) consists of a coordinate address, used to look up the coordinates of that atom; a pair type (j atoms only), which identifies the type of interaction which that j atom forms with the most recent i atom; and an ij bit, which identifies the atom as an i or j atom. The coordinate addresses are fed simultaneously to three coordinate memories (x, y, and z). These coordinates are passed to one of the inputs of three subtractors. If the atom is an i atom, nothing happens except that an empty cycle is generated. If the atom is a j atom, the subtraction is done to form delta-x, delta-y, and delta-z. These are squared and summed to form delta-r, squared, which is used as input to a table look-up to obtain the value of an interpolation function, which in the present invention is a square root table yielding r. This r, along with the pairtype which describes what kind of pair of atoms this ij pair is, is then used to look up the value of the energy and the value of F/r. The Cartesian components of the force vector are obtained by multiplying F/r by delta-x, delta-y, and delta-z, and the total energy and the force vector memories are updated.

In order to limit the total size of memory, the energy and the value of F/r are both calculated as a sum of two contributions, i.e. as $E = a(pt)*Ea(pt,r) + b(pt)*Eb(pt,r)$, where pt is the pair type and r is the scalar distance between the atoms comprising the pair. Since all function evaluations, including the square root, are handled by table lookups, this device is memory intensive. More specifically, as shown in FIG. 2, the coefficient tables and interpolated tables are accessed or addressed by the pair-type (pt) information acting as retrievable identifiers, so that the proper coefficient corresponding to the particular pair-type under scrutiny is read out from the table. Overall, there are about 5-10 Mbytes of memory distributed, throughout the system when it is equipped to handle 16,000 atoms and 1,000,000 interacting pairs. Note that if all hydrogens are included in the calculations, 16,000 atoms might require of the order of 1.5 million interacting pairs. The system has been designed so that additional pair list memory can be added at any time.

Each of the table look-ups is done by quadratic interpolation, as shown in FIG. 3. In each bin, the value of the function, the first derivative, and half of the second derivative are stored. The incoming value of the independent variable is scaled, integerized, and split into high and low order bits. The high order bits are added to an offset which is looked up as a function of the pair type and which gives the starting address of the table associated with that pair type. This sum is used to fetch the value, slope, and half of the second derivative from the tables, and these are used to compute:

$$y = y_0 + (dx)(y' + dx(y''))$$

The energy and force calculator described above has been designed to evaluate pairwise, central forces between objects in three dimensional space only. In the empirical Hamiltonian which is usually manipulated in molecular mechanics calculations, there are additional terms associated with bond angle bending, torsional excursions, and out-of-plane excursions which are not pairwise and central. The angle bending terms have been centralized by placing a non-Hooks law spring between atoms 1 and 3 in a 1-2-3 atom triplet which maps out the angular dependence normally used. This introduces a maximum error of 10% at 10 kt. The torsional terms can be handled in one of two ways: first, by positioning a point in space away from the 1-2-3-4 quadruplet using atoms 1,2 and 3 and rigid springs and subsequently dropping a non-Hooks law spring to mimic the torsional potential for excursions of the 4th atom; and second, by calculating these torsional contributions in the array processor which would otherwise be idle during the time the force and energy accumulator is working.

The length of the pipe is several hundred cycles, since each Weitek chip is 9 cycles deep internally. This effectively limits the minimum size the problem which is worth running of on this device, since a problem involving several hundred pairs would incur an effective overhead of a factor of two. However, this overhead is insignificant for typical problems involving proteins or DNA, since the number of pairs for these problems is typically two orders of magnitude greater than the length of the pipe. For any problem, once the pipe is full, a pair is evaluated every 100ns. This speed can be compared to that which is available on several general purpose machines; on a VAX 780 with a floating point accelerator, a pair can be evaluated every 150 μs using assembler code. On a Cyber 205, a benchmark provided by Osguthorpe et al (Osguthorpe, D.G., P. Dauber-Osguthorpe, Kitson, D., Wolff, J. and Hagler, A.T., A State of the art Calculation of a Biological System using a Cyber 205 Supercomputer), achieves the evaluation of a pair every 600ns but only if there is no pair list and all pairs are evaluated. On a Star ST100 array processor, it is possible to evaluate a pair every 1-2 μs using microcoded routines with a pair-list.

The device of this invention has been designed around the idea of easy maintainability. All tables are connected to a slow bus (Q bus) and can be down loaded either from the host VAX or through a resident Motorola 68010 microprocessor. The system is designed so that a single step mode is available for debugging, with selected pipeline registers readable from the slow bus. The hardware is being implemented in 6 layer DEC boards (13"×18"), with interboard connections implemented through the back plane and via ribbon cable. There are approximately 20 different board types.

The array processor chosen to complement this device is the Star ST100. The Star ST100 is presently the fastest commercially available array processor, with a theoretical rating of 100 Mflop. One feature of this machine which is crucial to this application is its ability to communicate with this device at a high rate, along with its ability to overlap communications and calculations. A crucial performance number for the array processor is the time required to evaluate a torsional couplet and resolve the forces into Cartesian components on each of the four atoms. This involves four square roots or divides, along with about 35 multiplies or adds. The ST100 is capable of evaluating a torsional couplet as a pipelined routine in 1.6 us, which is roughly ten times faster than its nearest presently available competitor. It is sufficiently fast to allow evaluation of torsional and angle bending terms during the time this device is evaluating the non-bonded pairwise central terms for most systems of biological interest.

Another crucial task assigned to the array processor is the updating of the pair-list. The pair-list is separated into two different parts containing fixed and variable pairs. The fixed pairs reflect the chemical connectivity of the atoms and thus do not change as the positions of the atoms move during the calculations. The variable pair-list is the one which is recalculated in the array processor after a number of iterations of the coordinate updates. The fixed pairlist is calculated once in the host and only changed by it if the connectivity changes. The structure of the Star ST100 permits rapid generation of the variable pair-list. Although the details of the algorithm are flexible and change as, for example, boundary conditions change, a pair of atoms can be considered and accepted a lying within as cutoff in 3 equivalent cycles (3 pairs in 9 cycles; each cycle in the ST100 is 40 ns).

The speed of this device as measured in megaflops/sec (m flops) is simple to determine. The Weitek computing chips perform one floating point operation every clock cycle (100ns); that is, they operate at the rate of 10 m flops each. There are about sixty Weitek chips in FASTRUN; thus, it operates at a speed of 600 m flops once the pipe is full. Note that, as discussed above, it takes several hundred cycles to fill the pipe. For a typical problem involving protein and solvent, this represents an overhead of about one percent. There is also an overhead associated with the introduction of each i atom into the pipe, since this generates an empty cycle. Since each i atom is followed in practice by 50 to 100 ]atoms (depending on the cutoff used), this represents a one to two percent overhead to the operation of the device of this invention. The total fraction of running time (i.e., duty-cycle for this device) varies depending on what algorithm is being used in the STAR to update the coordinates. However, it would be above 70% for molecular dynamics using Verlet integration, conjugate gradient energy minimization, and most Monte Carlo schemes.

There are several ways in which future systems using a similar architecture can be made faster. The most obvious is to use faster calculating chips along with faster memory, and this will certainly happen as the technology develops. In addition, one can consider ways in which some aspects of the calculations can be done in parallel without duplicating all of the memories. However, at this time, it is not obvious that it would be practical to install more than four memory shared parallel pipes with the present architecture. Thus, one can see ways of getting to several gigaflops in computing speed but much faster systems would probably require a very high order of parallelism in a very different architecture.

An orthogonal future development might involve the installation of 64 bit multipliers and adders as they become cost competitive at 100 ns speeds. There are applications which would gain significantly by this increase in precision. The development of a 64 bit machine, while not trivial since all pathways and memories double in size, is feasible and would be strongly aided by the prior development of a 32 bit/64 bit hybrid; that part of the calculation which is most prone to accumulated error, the summing of the forces and energies, is done to 64 bit accuracy.

REFERENCES

1. Go, W., Ann. Rev. Bioph. Bioeng. 12, 183 (1983).
2. Physics Today, 35, 6 (June 1983)
3. Wumthrich, K., Billeter, M., Braun, W.J., Mol. Biol. 196, 13, 42 (1983).
4. Schoenborn, B. and Kunes, A., Ann. Rev. Biophys. Bioengineer. 1:52.9 (1972)
5. Schoenborn, B. Brookhaven Symp. Biol. 27: II 3-II II (1976).
6. Schoenborn, B., Trends in Biochemical Sciences, 2, 206 (1977).
7. Schoenborn, B., Schneider, D., and Wise, D., ACA Transaction 19 (1983).
8. Mc Cammon, J., Wolynes, P., and Karplus, M., Biochemistry 18:6, 927 (1979).
9. Mc Cammon, J., Gelin, D.R., Karplus, M. Nature, 267,587 (1977).
10. Stillinger, F.N. Rahman, A.J., Chem., Phys., 60, 1545 (1974).
11. Pern, B., Ed. Modern Theoretical Chemistry, Volume 6, Plenum Press, New York (1980).
12. Wipff, G., Dearing, A., Weiner, P., Blaney, J., Kollman, P., J. Am. Chem. Soc. 105, 997 (1983).
13. Pincus, M., Burgess, A., Scheraga, H., Biopolymers 15, 2485 (1976).
14. Wodak, S.N. Janin, J., J. Mol. Biol., 124, 323 (1978).
15. Kaaartinen, M., Griffiths, G., Markham, G., and Milstein, C., Nature 304, 320 (1983).
16. Cleveland, M., Slatin, S., Finkelstein, A., and Levinthal, C., Proc. Natl. Acad. Sci. 80, 3706 (1983).
17. Berens, P. and Wilson, K, J. Comp. Chem, July, 82.
18. Brooks, B. Brucollori, R., Olafson, B., States, D., Fwaminathan, S., Karplus, M., J. Comp. Chem., 4, 187 (1983).
19. Hille, B., Ann, Rec. Physiol. 38:139, 52 (1976).

What is claimed is:

1. A computing device which calculates the total energy and total pairwise, central forces between selected pairs of discrete, interacting particles within a system which comprises
   a. means for generating as digital outputs both (i) a retrievable identifier of the spatial coordinates (x, y, z) for all selected pairs of particles i and j which interact with one another within the system and (ii) retrievable identifiers of the type of pairs, central interaction between each ij pair;
   b. means for (i) inputting digital outputs from the generating means, (ii) determining therefrom $r^2$, the square of the radius vector between each i and j, by calculating solutions for the equation $$r^2 (x_i-x_j)^2+(y_i-y_j)^2+(z_i-z_j)^2,$$

where $(x_i, y_i, z_i)$ and $(x_j, y_j, z_j)$ are the spatial coordinates for i and j obtained as digital inputs from the generating means, and (iii) outputting $r^2$ values in digital word form;
   c. look-up means for (i) inputting $r^2$ values in digital word form, (ii) determining therefrom [r, the square root of $r^2$] respective values corresponding to a predetermined function of $r^2$, and (iii) outputting [r] said respective values in digital word form;
   d. means for (i) inputting the digital outputs of the generating means relating to the types of pairwise, central interactions and for inputting the [r] values from the [r determining] look-up means, (ii) calculating therefrom the energy and the force/r values for each ij pair of particles, and (iii) outputting the energy and force/r values for each ij pair of particles in digital word form;
   e. means for (i) inputting the force/r values from the force/r calculating means, (ii) determining therefrom the Cartesian components of the force on each particle i within each pair ij, and (iii) outputting the cartesian component values of the force between each particle pair ij in digital output form; and
   f. means for (i) inputting for each particle pair ij the energy values from the energy calculating means and the Cartesian component values of the force from the means for determining the total pairwise, central force values between each ij particle pair, (ii) accumulating the total energy values for each ij particle pair and the total force values between each particle pair ij, and (iii) outputting such total energy and total force values.

2. A computing device of claim 1, wherein the means for generating retrievable identifiers comprises a memory storage unit containing both (i) digital lists of particle indentifications and spatial coordinates for particles i and j which lists are accessible in response to the generation of digital words from an external index generator and (ii) the types of all pairwise, central interactions between particles i and j which types are accessible in response to the generation within the memory storage unit of words representing particles i and j.

3. A computing device of claim 1, wherein said predetermined function is the square root of $r^2$ and the look-up means comprises a memory storage unit containing in digital form a table of square root values for any $r^2$, which table is accessible in response to digital word input of $r^2$.

4. The mechanics computing device of claim 1, wherein the particles comprise atoms.

5. A computing device of claim 1, wherein the means for calculating $r^2$ comprises subtractors for receiving the spatial coordinates (x, y, z) for each selected ij pair from the means for generating and producing respective outputs $(x_i-x_j)$, $(y_i-y_j)$, $(z_i-z_j)$, fed to multipliers for squaring each subtractor output.

6. A computing device of claim 5, wherein said predetermined function is the square root of $r^2$ and the look-up means comprises a memory storage unit containing a digital table of square root values for any $r^2$, which unit is accessible in response to digital inut values of $r^2$.

7. A computing device of claim 1, wherein the means for calculating the energy and force/r values for each ij pair contains coefficient tables describing each ij pair type and quadratically interpolated tables describing each ij pair type and the value of r, respectively, the coefficient tables are accessible in response to digital inputs representing the retrievalbe identifiers from the means for generating and the interpolated tables are accessible in response to digital inputs representing the retrievable identifiers from the means for generating and also to r values and provide digital input to a combination of multipliers and adders describing solutions to the formula for calculating energy:

E = Cf1(pt) Table 1(pt,r) + Cf2(pt) Table 2(pt,r)

and solutions to the formula for calculating force/r:

F/r = Cf3(pt) Table 3(pt,r) + Cf4(pt) Table 4(pt,r).

8. A computing device of claim 7, wherein the means for calculating the energy and force/r values comprise a first memory storage unit containing a table of values of a function y; a second memory storage unit containing a table of values of y', the derivative of the function y; a third memory storage unit containing a table of values of y'', one half of the second derivative of the function y; the outputs of the second and third memory storage units are multiplied in respective multipliers by a value of r and the products added in adders with the output of the first memory storage unit so as to calculate the result of the equation:

$$y = y_0 + (d_x)(y' + d_x(y''));$$

the means for calculating further comprising an offset memory which is responsive to a retrievable identifier for reading out a starting point in each of the tables in the $y_0$, y', and y'' memories, the read-out starting point is fed to maximum and minimum memories containing respectively maximum and minimum bounds of the tables for determining whether the starting point is within the boundaries.

9. A computing device of claim 7, wherein the digital outputs from the means for calculating corresponding to solutions of the equation for calculating energy:

E = Cf1(pt) Table 1(pt,r) + Cf2(pt)*Table 2(pt,r)

comprise digital inputs to the means for accumulating total energy values that comprises an energy sum accumulator comprising a memory which sums total energies for each particle pair ij for reading out therefrom total energy values as digital inputs to an array processor.

10. A computing device of claim 7, wherein the means for calculating $r^2$ comprises subtractors for receiving the spatial coordinates (x, y, z) for each selected ij pair from the means for generating and producing respective difference outputs $(x_i-x_j)$, $(y_i-y_j)$, $(z_i-z_j)$ and wherein the digital outputs from the means for calculating corresponding to solutions of the equation for calculating force/r:

F/r = Cf3 (pt)*Table 3(pt,r) + Cf4 (pt)*Table 4(pt,r)

comprise digital inputs to the means for accumulating total force values that comprises a force/r accumulator comprising multipliers for multiplying the digital inputs by the difference outputs from the means for determining $r^2$, memories for accumulating the products from the multipliers, and adders which sum the Cartesian components of the force on each particle read out from the memories.

11. A computing device of claim 10, wherein the combination of multipliers and adders are accessible in response to a pair of digital word inputs describing a force/r value and a value of one spatial coordinate (delta x, delta y or delta z) for a pair of particles ij, multiply the values of the pair of digital word inputs to obtain a product (force/r)(delta x) or (force/r)(delta y) or (force/r)(delta z), add the product so obtained to a product previously obtained for any i, add the negative value of that product to a product previously obtained for j, and sum the accumulated force/r values for i and j.

12. A computing device which calculates the total energy and total pairwise, central forces between selected pairs of discrete, interacting atoms comprising:
   a. a storage device containing words for forming an ordered list of pairs of atoms (i,j) that can interact with one another, and wherein each word in the list is formed of an i/j bit indicating whether an atom of a pair is an i or a j atom, an atom number uniquely identifying each atom, and a pairtype number pt identifying an interaction that a particular j atom undergoes with an i atom of a pair;
   b. means for selectively reading out said atom numbers from said storage device to form said pairs of (i,j) atoms from said atom numbers, wherein j is an atom number greater than i;
   c. a plurality of coordinate memories containing cartesian coordinates of all atoms identified in said storage device, said coordinate memories being addressed by said i, j atoms arranged in pairs formed of said atom numbers selectively read out from said storage device for reading out the x, y and z cartesian coordinates of the atoms;
   d. arithmetic means for producing the square of the difference between each respective x, y, z cartesian coordinates of the pairs of i,j atoms read out from sai plurality of coordinate memories;
   e. summing means for summing said squares of the difference produced by said arithmetic means;
   f. look up table means containing values for determining a function of the square of the radial distance between each atom of an i,j pair and being arranged to be addressed by the output of said summing means;
   g. a plurality of coefficient memories containing information relating to the electrical charges on each atom and van der Waals interactions and being addressed by said pair type numbers read out from said storage device;

h. a plurality of energy tables containing information relating to the energy of each atom and being addressed by said pair type numbers read out from said storage device and said values for determining a function of the square of the radial distance read out from said look-up table means;

i. a plurality of force divided by radial distance tables containing information relating to the ratio of the atomic forces divided by the radial distance between the atoms of an i,j pair and being addressed by said pair type number read out from said storage device and said values for determining a function of the square of the radial distance read out from said look-up table means;

j. arithmetic means for producing an energy sum of the product of the output from a coefficient table and a respective energy table, said energy sum representing the energy on an i atom created by a j atom of and i,j pair and for producing a force sum of the product of the output from a coefficient table and a respective force divided by radial distance table, said force sum representing the force exerted on an i atom by a j atom of an i,j pair;

k. accumulator means for accumulating the energy values produced by said arithmetic means and producing a total energy value therefrom;

l. coordinate component determining means receiving said force sum and said difference between each respective x, y, z cartesian coordinates from said arithmetic means for producing a Cartesian coordinate force value; and m. force accumulator means for accumulating Cartesian coordinate force values from said coordinate component determining means in response to said atom numbers from said storage device and producing an x, y, z component of said force sum.

* * * * *